United States Patent [19]

Yamada et al.

[11] Patent Number: 4,954,443

[45] Date of Patent: Sep. 4, 1990

[54] METHOD OF IMMOBILIZING BIOCHEMICALLY ACTIVE SUBSTANCE WITH XANTHAN GUM

[75] Inventors: Osamu Yamada; Tadasu Fujita, both of Yokohama, Japan

[73] Assignee: The Nisshin Oil Mills, LTD., Tokyo, Japan

[21] Appl. No.: 274,604

[22] Filed: Nov. 18, 1988

Related U.S. Application Data

[63] Continuation of Ser. No. 810,600, Dec. 19, 1985, abandoned.

[30] Foreign Application Priority Data

Dec. 27, 1984 [JP] Japan ............................... 59-273786
Feb. 12, 1985 [JP] Japan ................................. 60-24988

[51] Int. Cl.$^5$ ...................... C12N 11/10; C12N 11/02; C12N 11/04
[52] U.S. Cl. .................................... 435/178; 435/177; 435/182; 530/813
[58] Field of Search ............... 435/174, 177, 178, 182; 530/813

[56] References Cited

U.S. PATENT DOCUMENTS

| 3,841,969 | 10/1974 | Emery et al. | 435/178 X |
| 4,138,292 | 2/1979 | Chibata et al. | 435/178 |
| 4,352,883 | 10/1982 | Lim | 435/182 X |
| 4,391,909 | 7/1983 | Lim | 435/182 X |
| 4,407,957 | 10/1983 | Lim | 435/178 |

*Primary Examiner*—David M. Naff
*Attorney, Agent, or Firm*—Bacon & Thomas

[57] ABSTRACT

Enzymes or microorganisms are immobilized by bringing a first aqueous solution into contact with a second aqueous solution containing metal ions having a valence of 3 or more. The first solution contains enzymes or microorganisms, and at least one immobilizing agent selected from the group consisting of Xanthan gum and derivatives thereof. The immobilizing agent is thereby hardened in a state to enclose the enzymes or microorganisms. Preferably, the metal ions are iron, tin, manganese or titanium ions.

11 Claims, No Drawings

METHOD OF IMMOBILIZING BIOCHEMICALLY ACTIVE SUBSTANCE WITH XANTHAN GUM

This application is a continuation of application Ser. No. 810,600, filed 12/19/85 now abandoned.

BACKGROUND OF THE INVENTION

1. Field of the Invention

The present invention relates to a method of immobilizing a biochemically active substance and, more particularly, to a method of immobilizing a biochemically active substance using an immobilizing agent derived from a naturally occurring material.

2. Description of the Prior Art

Substances useful in the medicine, food, and chemical industries have recently been produced using biochemically active substances such as enzymes and microorganisms.

Many studies have been recently made in an attempt to increase production yield of such useful substances by using enzymes or microorganisms immobilized on carriers. Production of useful substances using immobilized enzymes include optical resolution a of DL-amino acid with aminoacylase, production of isomerized sugar with glucose isomerase, production of L-malic acid with fumarase, and production of low-lactose milk with $\beta$-galactosidase. For production of useful substances using immobilized microorganisms, studies are being made on the production of ethanol with an alcohol yeast, production of acetic acid with a strain of genus Acetobacter, production of lactic acid with a strain of genus Lactobacillus, and production of n-butanol and isopropanol with a strain of genus Clostridium. Examples using immobilized animal/plant cells include production of digoxin with Digitalis lanata and production of anthraquinones with Morinda citrifolio.

Biological species or biochemically active substances such as enzymes or microorganisms or cells are immobilized on carriers through adsorption, bonding, crosslinking, or gel enclosure. Examples of carriers include polyacrylamide, polyvinyl alcohol, polyvinyl chloride, ion exchangers, magnetic bodies, semipermeable membranes, cellulose, agar, collagen, alginates, gelatin, and carrageenan.

The conventional immobilizing methods do, however, have various inherent problems. Such problems include a hygienic problem induced by mixing in of a trace amount of a monomer in a sample, removal of a biological species by insufficient adsorption, or deactivation or death of the biological species on heat treatment. Thus, these conventional methods cannot provide satisfactory results.

SUMMARY OF THE INVENTION

It is, therefore, an object of the present invention to provide a method which can immobilize a biochemically active substance easily and economically, by using a safe, stable immobilizing agent.

According to the present invention, there is provided a method of immobilizing a biochemically active substance, comprising:

bringing a first aqueous solution into contact with a second aqueous solution containing metal ions having a valence of 3 or more, the first solution containing at least one biochemically active substance and at least one immobilizing agent selected from the group consisting of Xanthan gum and derivatives thereof, thereby hardening the immobilizing agent in a state to enclose the biochemically active substance; and immobilizing the biochemically active substance in the hardened immobilizing agent.

DETAILED DESCRIPTION OF THE PREFERRED EMBODIMENTS

Biochemically active substances immobilized by the method of the present invention are substances which can produce useful substances upon biochemical reaction. Such biochemically active substances include enzymes, microorganisms, animal/plant cells, and protoplasts.

Enzymes utilizable in aqueous and non-aqueous reaction systems can be used. Examples of enzymes which can be utilized in aqueous reaction systems include isomerases such as glucose isomerase; hydrolase such as invertase, urease, protease, or lipase; and lactose decomposing enzymes such as $\alpha$-galactosidase or lactase ($\beta$-galactosidase). Examples of enzymes which can be utilized in non-aqueous reaction system include lipase, used for manufacturing cacao-substitute oils and fats by interesterification of animal/plant oils and fats.

Microorganisms can be any microorganisms which produce useful substances outside themselves, e.g., yeasts, molds, and bacteria. Examples of such microorganisms include Saccharomyces cerevisiae (NRRL Y-1531, IFO 03309), which produces ethanol; Clostridium butyricum (IFO 3315, ATCC 6014), which produces isopropanol and n-butanol; a strain of genus Xanthomonas which produces Xanthan gum, e.g., Xanthomonas campestris (NRRL B-1459, IFO 13551), Xanthomonas begoniae, Xanthomonas incanae, Xanthomonas translucens (IFO 13558, IFO 13559), Xanthomonas phaseoli (IFO 13553, IFO 13554), and Xanthonomas carotae (Japanese Patent Publication No. 45-31346); a strain of genus Lactobacillus which produces lactic acid, e.g., Lactobacillus lactis (IAM 1317, NRRL B-736, etc.); Arthrobacter oxydans (ATCC 14358, etc.); and Aspergillus niger (ATCC 10577, ATU A-9-9, IAM 2093, etc.), which produces citric acid. However, microorganisms need not be limited to these examples.

Enzymes are industrially useful substances and therefore microorganisms producing such enzymes can also be used in the present invention. Examples of such microorganisms include a strain of genus Candida which produces lipase, e.g., Candida cylindracea (ATCC 14830, etc.) or Candida paralypolytica (Agr. Biol. Chem., 32 (3), 390–391, 1968); a strain of genus Rhizopus, e.g., Rhizopus arrhizus (IAM 6056, IFO 5780, etc.), Rhizopus delemar (IFO 4730, etc.) or Rhizopus japonicus (IFO 5319, AHU 6525, etc.); a strain of genus Mucor, e.g., Mucor miehei (IFO 9740), Mucor javanicus (AHU 6010, OUT 1051-1058, IFO 4569, etc.), or Mucor pusillus (IFO 4578, HUT 1185-1187, etc.); a strain of genus Aspergillus, e.g., *Aspergillus niger* (IFO 4414, etc.); and a strain of genus Geotrichum, e.g., *Geotrichum candidum* (IFO 5368, OUT 4027-4030, etc.). Strains of genus Aspergillus which produce amylase include *Aspergillus oryzae* (IAM 2736, etc.) and *Aspergillus niger* (IAM 3008, NRRL 337, etc.). Strains of genus Bacillus which also produce amylase include *Bacillus amyloliquefaciens* (IAM 1521-1523, etc.) and *Bacillus licheniformis* (IFO 12195-12197, etc.) Strains of genus Aspergillus which produce protease include *Aspergillus oryzae* (IAM 2609, IAM 2649, etc.) and *Aspergillus melleus* (IFO 4339, IFO 4420, IAM 2064, etc.). Strains of genus Rhizopus which also produce protease include

*Rhizopus niveus* (IFO 4759, OUT 1187, etc.) These and other microorganisms, such as variations, nutritional mutants, and drug resistant mutants thereof, can be used as the biochemically active substances in the method of the present invention.

According to the present invention, an immobilizing agent for immobilizing a biochemically active substance is Xanthan gum and/or derivatives thereof. Xanthan gum is a water-soluble polymeric polysaccharide obtained by fermentation of a Xanthomonas microorganism. For example, Xanthan gum is manufactured by culturing *Xanthomonas campestris* (NRRL B-1459, IFO 13551, etc.), *Xanthomonas translucens* (IFO 13558, etc.), and *Xanthomonas phaseoli* (IFO 13553, etc.). Culturing is performed under aerobic conditions at 25° to 30° C., using a culture medium containing a carbon source (e.g., glucose, sucrose, or theriac), a nitrogen source (e.g., an ammonium salt, peptone, or yeast extracts), and trace amounts of metal ions.

Xanthan gum is normally recovered by sterilizing the cultured medium, precipitating it with a lower alcohol such as ethanol or isopropanol, or with polyvalent metal ions, and then drying the precipitate. Xanthan gum manufactured in this manner is assumed to have a molecular structure wherein a pyruvate or an acetate is bonded to a main chain structure of D-glucose, D-mannose and glucuronic acid, and is also assumed to have a molecular weight of about 2,000,000.

Usually, Xanthan gum is a mixture of a potassium salt, a sodium salt and a calcium salt, and is a water-insoluble viscous polysaccharide. Xanthan gum has favorable properties such as an excellent viscosity increasing function, an excellent emulsification-stabilization function, an excellent dispersion effect on particles or air bubbles, and excellent stability against temperature or pH changes, and against various salts. Therefore, Xanthan gum is widely used as an additive in various industries, such as the food, paint, and papermaking industries, and in oil drilling.

The low toxicity of Xanthan gum for animal and human has been demonstrated. Xanthan gum is designated as a safe additive by the W.H.O. and the U.S. FDA, and is used domestically (Japan) in foodstuffs. Furthermore, Xanthan gum is extremely stable against decomposition by various enzymes such as amylase, protease, lipase, or cellulase.

According to the method of the present invention, a Xanthan gum which has such low toxicity and excellent stability against enzymes, or a derivative of such a Xanthan gum, is used as an immobilizing agent. Examples of derivatives of Xanthan gum include a derivative obtained through deacetylation of O-acetyl groups in the Xanthan gum molecules (Japanese Patent Disclosure No. 59-142201), a derivative having a low pyruvate content (Japanese Patent Disclosure No. 58-21403), a derivative containing no pyruvic acid (Japanese Patent Disclosure No. 56-85293 and No. 56-85284), and a derivative having a low Ca content (Japanese Patent Disclosure No. 54-15800). Guar gum or locust bean gum can be added in order to increase viscosity and gel strength of the Xanthan gum.

In order to immobilize a biochemically active substance, a first aqueous solution containing Xanthan gum and/or its derivatives and a biochemically active substance is brought into contact with a second aqueous solution containing metal ions having a valence of 3 or more.

When the biochemically active substance is an enzyme, the first aqueous solution is prepared by dissolving a powdered enzyme and a Xanthan gum and/or Xanthan gum derivative powder in water.

When the biochemically active substance is a microorganism, the selected microorganism is cultured on a culture medium suited thereto, to an exponential growth phase or resting stage. The cultured medium containing the microorganism and/or the microorganism separated from the water medium by centrifugation is mixed with an aqueous solution of Xanthan gum and/or a Xanthan gum derivative, together with, if required, another portion of a culture medium having the same composition as the medium used, so as to prepare the first aqueous solution.

The first aqueous solution generally contains the immobilizing agent (Xanthan gum and/or a derivative thereof) at a concentration of 0.01% to 15% and preferably 0.5 to 7%. When the concentration of the immobilizing agent is less than 0.01%, the immobilizing agent is too diluted and does not precipitate, so that it cannot immobilize the biochemically active substance. On the other hand, when the concentration of the immobilizing agent exceeds 15%, mixing it with the biochemically active substance or mixing the obtained solution with water becomes difficult and prevents preparation of a desirably immobilized biochemically active substance.

When guar gum or locust bean gum is added, its amount is usually to be 10% to 80% and preferably 20% and 70%, based on the weight of the Xanthan gum or its derivative. Specifically, guar gum is usually used in an amount of 10 to 80%, preferably 25 to 75% of the total weight of the immobilizing agent plus guar gum, in which the immobilizing agent usually occupies 90 to 20%, preferably 75 to 25%. Locust bean gum is usually used in an amount of 10 to 80%, preferably 20 to 70% of the total weight of the immobilizing agent plus locust bean gum, in which the immobilizing agent usually occupies 90 to 20%, preferably 80 to 30%.

As has been described earlier, the second aqueous solution contains metal ions having a valence of 3 or more. Examples of such metal ions include Al ions, Fe ions, Sn ions, Pb ions, Mn ions, Cr ions, Ti ions, and the like. These metal ions can be supplied from a corresponding water-soluble metal salt. Examples of such salts include halides (chlorides, bromides, or iodides), oxides, hydroxides, nitrates, sulfates, carbonates, phosphates, acetates, complex compounds, and chelate compounds. One or more types of such salts can be used.

The second aqueous solution contains the metal ions at a concentration sufficient to allow precipitation of the immobilizing agent. Such a concentration is preferably 0.01 to 20%. When the concentration of the metal ions is less than 0.01%, the immobilizing agent cannot completely precipitate and the yield is lowered. On the other hand, if the concentration of the metal ions exceeds 20%, the presence of an excessive amount of the metal ions may adversely influence activity of the biochemically active substance.

The second aqueous solution can further contain metal ions having a valence of 2, if needed. Examples of metal ions having a valence of 2 include Ca ions, Mg ions, Zn ions, Cu ions, and Fe ions. Metal ions having a valence of 2 can be supplied from corresponding water-soluble salts, as described with respect to the metal ions having a valence of 3 or more. When metal ions having a valence of 2 are used, they are to be in a concentration of 0.01% to 10% and preferably, 0.1% to 5%.

The two aqueous solutions are brought into contact and mixed at a temperature of 5° C. to 75° C. According to the present invention, various immobilized substances can be prepared in accordance with the particular method of bringing the two solutions into contact with each other. When the first aqueous solution is dripped or sprayed into the second aqueous solution, the immobilizing agent gels and precipitates in a manner in which the agent encloses the biochemically active substance. More specifically, when the first solution is sprayed into the second solution through a thin nozzle, a crystalline or fibrous immobilized substance containing no water results. When the first solution is dripped into the second solution, a bead-like and spherical immobilized substance can be obtained which has water-containing gels in its molecular structure. When the biochemically active substance is an enzyme, if the latter method is adopted, an optimal pH of the enzyme can be obtained even in a non-aqueous reaction system (reaction in an organic solvent) and optimal conditions for enzyme reactions can be obtained (See Example 2 below). When the concentration of the immobilizing agent in the first solution is changed within the above-mentioned range, immobilized substances having various degrees of density can be obtained; i.e., soft to hard immobilized substances can be obtained.

When a precipitate is prepared in this manner, it is recovered by filtration or the like, and rinsed with water to remove any excess metal ions. Thus, a desired immobilized biochemically active substance is obtained.

EXAMPLE 1

Five grams of Xanthan gum (trade name: "KEL-TROL", available from Kelco Co., U.S.A.) were dissolved in 200 ml of ion-exchanged water to prepare a gel-like aqueous solution. Meanwhile, 3 g of lipase (trade name: "Lipase OF", available from Meito Sangyo K.K., Japan) were dissolved in 10 ml of ion-exchanged water. The two solutions were agitated and then mixed at room temperature. The resultant solution was dripped, under mild agitation, into a 0.5% ferric chloride aqueous solution and a precipitate was obtained. After filtering out the precipitate with a paper filter, it was washed with ion-exchanged water to provide spherical immobilized lipase.

Fifty grams of the immobilized lipase (0.3% based on the substrate content) were mixed with 100 g of olive oil, 100 ml of 0.1M phosphate buffered solution (pH 6.0), and 2 g of polyvinyl alcohol (molecular weight: 1,750). After the mixture was emulsified, hydrolysis of the olive oil was performed at 37° C. When the mixture was allowed to react for 4 hours, the rate of hydrolysis was 95% (calculated from the acid value measurement of free aliphatic acids).

As a control, the same procedures as above were followed, except that free lipase was used in place of the immobilized lipase of the present invention. In the Control, the hydrolysis rate after 5 hours was 94%.

When the immobilized lipase already used in the hydrolysis reaction was recovered by filtration and then subjected to the same procedures again, the hydrolysis rate after 5 hours was 75%. This confirmed the fact that immobilized lipase can be reused.

COMPARATIVE EXAMPLE 1

Hydrolysis of olive oil was performed following the same procedures as in Example 1, except that Xanthan gum was replaced with κ-karageenan and an immobilized lipase was obtained by a known method (Saburo Fukui et al., "Koso-Kogyo", Tokyo Kagaku Dojin, p. 169, 1981). The hydrolysis rate was 60%, which is significantly lower than that of Example 1.

EXAMPLE 2

Ten grams of Xanthan gum (food grade, available from Rone Pulane Co., France) and 5 g of lipase (derived from Rhizopus delemar and available from Seikagaku Kogyo K.K., Japan) were mixed at room temperature to prepare a powder mixture. The powder mixture was gradually added to 300 ml of a 0.3M phosphate buffered solution (pH 5.5) to prepare a gel-like aqueous solution. The obtained solution was dripped into a 1% aqueous solution of calcium chloride and aluminum phosphate (1:1) under agitation, to provide a bead-like precipitate. After the precipitate was filtered out with a paper filter, it was washed with a 0.3M phosphate buffered solution (pH 5.5) to obtain bead-like immobilized lipase which maintained gel form.

A hundred grams each of olive oil and palmitic acid were dissolved in 350 ml of n-hexane, and 40 g of the immobilized lipase (0.5% based on the substrate content) were added. The mixture was slowly agitated at 35° C. to allow interesterification. The triglyceride composition ratio of the reaction product determined by gas chromatography after 5 hours indicated that triolein (a, non-substituted product): dioleylmonopalmitin (b, mono-substituted product): monooleyldipalmitin (c, di-substituted product): tripalmitin (d, tri-substituted product) was 25:45:28:2.

As a Control, when free lipase was used in place of the immobilized lipase, the triglyceride composition ratio a:b:c:d was determined to be 49:30:21:0. These facts demonstrate advantageous properties of the immobilized lipase of Example 2.

EXAMPLE 3

Five grams of Xanthan gum (trade name: "KEL-TROL", available from Kelco Co., U.S.A.) were mixed with 1 g of α-galactosidase (reagent available from Sigma Chemical Co., U.S.A.) The mixture was added to 100 ml of ion-exchanged water at room temperature, to provide a gel-like aqueous solution. A 0.7% ferric chloride aqueous solution was sprayed into the first mixture through a thin nozzle, under pressure, and a flaky crystalline precipitate was obtained. After the precipitate was recovered by filtration, it was washed with ion-exchanged water, and dried with air, to provide crystalline immobilized α-galactosidase.

Three grams of the immobilized α-galactosidase were added to 100 ml of soybean milk (available from NISSHIN OIL MILLS, LTD., Japan) and the mixture was agitated at 25° C. When the reaction product was analyzed after 4 hours by gas chromatography, fract oligosaccharides in soybean milk, including raffinose and stachyose, were decreased in amount and monosaccharides including galactose or glucose were detected. Thus, enzyme activity of the immobilized α-galactosidase was confirmed.

EXAMPLE 4

One gram of 0-deacetylated Xanthan gum derivative prepared by a method described in Japanese Patent Disclosure No. 59-142201, and 0.25 g of invertase (derived from Candida utilis, available from Seikagaku Kogyo K.K., Japan) were mixed at room temperature to provide a powder mixture. The powder mixture was added to 20 ml of ion-exchanged water to provide a gel-like aqueous solution. The solution was sprayed into a 0.5% ferric chloride aqueous solution through a thin nozzle, to prepare a fibrous precipitate. After the precipitate was filtered out, it was washed with ion-exchanged water to provide fibrous, water-containing immobilized invertase.

Five grams of the immobilized invertase were added to a 10% sucrose aqueous solution and the mixture was stirred at room temperature. When a reduced sugar (glucose) was detected using a glycosuria reagent test paper strip (trade name: "Tes Tape", available from Shionogi and Co., Ltd. Japan), the immobilized invertase was shown to exhibit enzyme activity.

EXAMPLE 5

Bead-like immobilized protease was prepared following the same procedures as in Example 2, except that the lipase was replaced with protease (trade name: "Bioprase", available from Nagase Seikagaku Kogyo K.K., Japan), the 0.3M phosphate buffered solution (pH 5.5) was replaced with a 0.3M boric acid/sodium carbonate buffered solution (pH 8.0), and aluminum phosphate was replaced with tin sulfate dihydrate.

Using 2 g of the immobilized protease (1% based on the substrate content) and 5 g of milk casein, enzyme activity was examined by the Folin method (See J. Biol. Chem., 73, 627, 1929) at 50° C. and pH 8.0. Substantially the same activity as in the Control only using protease was exhibited.

EXAMPLE 6

Following the same procedures as in Example 2, bead-like immobilized lipase was prepared. More specifically, 10 g of Xanthan gum (trade name: "KELTROL", available from Kelco Co., U.S.A.) and 7 g of lipase (derived from Mucor miehei and available from Nobo Industries Co., Denmark) were dissolved in 300 ml of a 0.4M phosphate buffered solution (pH 7.5) to provide a gel-like aqueous solution. The solution was sprayed from an ultrafine nozzle to cause precipitation in a 0.5% calcium chloride aqueous solution and then in a 0.3% ferric chloride aqueous solution. After filtration, the precipitate was washed with a 0.4M phosphate buffered solution (pH 7.5) and dried with air to provide bead-like immobilized lipase.

180 g of the immobilized lipase were packed in a glass tube having an inner diameter of 20 mm and a length of 50 cm, to prepare a column of immobilized lipase. A solution prepared by dissolving 10 g each of triolein and stearic acid in 40 ml of n-hexane was kept at 40° C. and pumped into the immobilized lipase from the lower portion of the column at a flow rate of 10 ml/hour. The solution flowing out of the column was recovered and the triglyceride composition of the solution was determined by gas chromatography. The composition ratio of trolein:dioleylmonostearin:monooleyldistearin:tristearin was 37:44:19:0 after 4 hours, and 15:45:37:3 after 10 hours.

The following Examples were performed under aseptic conditions using clean benches.

EXAMPLE 7

Xanthomonas campestris (IFO 13551) was shaken-cultured in 200 ml of a culture medium containing 2.5% of glucose, 0.5% of potassium hydrogendiphosphate, 0.2% of peptone, 0.1% of magnesium sulfate, and 0.001% of ferrous chloride, at 27.5° C. for 5 days, to provide a cultured solution containing Xanthomonas campestris. 200 ml of a 2.5% Xanthan gum (trade name: "KELTROL", available from Kelco Co., U.S.A.) aqueous solution were mixed with the cultured solution. The resultant mixture was dripped into a 3% aqueous aluminum nitrate solution to allow a spherical, water-insoluble substance to precipitate. The precipitate was filtered out with a paper filter (No. 5B available from Toyo Roshi K.K., Japan), and the precipitate was washed with ion-exchanged water to remove excess metal ions and to obtain an immobilized material. Fifty grams of the immobilized material were added to 200 ml of a culture medium of the same composition as above and cultured for 5 days under the same conditions. As a result, a cultured solution having a viscosity of 7,500 cps/25° C. was obtained. After sterilization in an autoclave, the solution was centrifuged to separate out the immobilized material. When the Xanthan gum content of the resultant solution was examined by an ethanol precipitation method, it was found to be 1.5% by weight.

EXAMPLE 8

Xanthomonas campestris (NRRL B-1459) was cultured following the same procedures as in Example 7 to obtain 200 ml of a cultured solution. 20 ml of a culture medium of the same composition as in Example 7 and 200 ml of a 3.5% Xanthan gum (food "Grade", available from Rone Poulane Co., France) aqueous solution were added to the cultured solution and agitated. The resultant mixture was blown into an aqueous solution containing 3% of ferric chloride and 2% of calcium chloride through a thin nozzle (0.5 mm diameter) to allow a bead-like substance to precipitate. After the precipitate was filtered out, it was washed with water to provide an immobilized material. 200 g of the immobilized material were packed in a glass tube having an inner diameter of 2 cm and a length of 50 cm, to provide a column. 300 ml of the same culture medium as above with Xantamonas campestris were circulated by a liquid pump to culture at 25° to 30° C., a pH of 6.0 to 8.0 and an air flow speed of 5 l/min. for 6 days. Thereafter, another portion of the same culture medium was added at a rate of 1 ml/min. to obtain a cultured solution having a viscosity of 8,000 cps/25° C. The Xanthan gum content of the solution was found to be 1.8% by weight.

EXAMPLE 9

Saccharomyces cervisiae (IFO 0390) was cultured in 100 ml of a PGS culture medium (30 g of pressed yeast, 15 g of glucose, and 15 g of sucrose were added to an extract obtained by boiling 200 g of potatoes in 1 l of hot water, thereby obtaining 1 l of culture medium) at 30° C. for 4 days. 15 ml of another portion of the same culture medium and 100 ml of a 2% Xanthan gum derivative (deacetylated Xanthan gum prepared by the method described in Japanese Patent Disclosure No. 59-142201) were added to the culture and mixed well. The mixture was dripped into a 7% aqueous aluminum sulfate solution to allow a spherical, water-insoluble substance to precipitate. The precipitate was filtered out and then washed with water to provide an immobilized substance, as in Example 7. Fifty grams of the immobilized material were added to 100 ml of a 5% glucose aqueous solution. The resultant mixture was cultured by shaking at 30° to 35° C. for 24 hours. When the concentrations of glucose and alcohol in the cultured solution were measured by a commercially available kit (Boehringer Co.), they were found to be 3.5% and 0.4%, respectively.

EXAMPLE 10

Rhizopus delemar (IFO 4730) was cultured in 50 ml of a potato sucrose solution at 25° C. for 3 days. After adding 100 ml of an aqueous solution containing 3% of Xanthan gum (Kelco Co., U.S.A.) and 1% of guar gum or locust bean gum (food additive grade, available from K.K. Nichiei Chemical, Japan), the mixture was dripped into a 5% ferric chloride aqueous solution while stirring, to allow a bead-like, water-insoluble substance to precipitate. The precipitate was filtered out and washed with water to provide an immobilized material, as in Example 7. Thirty grams of the immobilized material were added to 30 ml of a 0.5M phosphoric acid buffered solution (pH 6), and thereafter 10 g of olive oil (neutralization number 0.1) and 1 g of polyvinyl alcohol were added. After the mixture was shaken at 30° C. for 24 hours, the acid value was measured to be 112. Thus, fat hydrolysis activity of the lipase immobilized in this manner was confirmed. Forty grams of the immobilized material were added to 10 g each of olive oil and palmitic acid dissolved in 40 ml of n-hexane, and allowed to interesterify at 30° to 35° C. while being stirred. When the triglyceride composition ratio of the reaction product was examined by gas chromatography, triolein (non-substituted product) : dioleylmonopalmitin (mono-substituted product) : monooleyldipalmitin (di-substituted product) : tripalmitin (tri-substituted product) was 60 : 28 : 12 : 0. Thus, interesterification activity of the lipase immobilized in this manner was confirmed.

EXAMPLE 11

Candida utilis (ATCC 16321) was cultured following the same procedures as in Example 9. 20 ml of another portion of the same PGS culture medium and 100 ml of an aqueous solution containing 1% of Xanthan gum (Kelco Co., U.S.A.) and 1% of deacetylated Xanthan gum (the same Xanthan gum as used in Example 9) were added to the cultured solution. The resultant solution was dripped into a 1% aqueous calcium chloride solution and then into a 2% aqueous aluminum phosphate solution through a thin nozzle to allow a bead-like substance to precipitate. The precipitate was filtered and washed with water to obtain an immobilized material. Thirty grams of the immobilized material were added to a 10% aqueous sucrose solution and the mixture was stirred at room temperature. After the immobilized material was filtered through a 0.22μ millipore filter, reduced sugar (glucose) in the precipitate was detected using a glycosuria reagent test paper strip (trade name: "Tes Tape", available from Shionogi & Co., Ltd., Japan). Thus, enzyme activity of the immobilized inverbase was confirmed.

EXAMPLE 12

Aspergillus oryzae (IAM 2649) was treated in the same manner as in Example 10 to obtain an immobilized material. Fifty grams of the immobilized material and 5 g of milk casein as a substrate were used, and resultant protease activity was examined at 50° C. by the Folin method (J. Biol. Chem., 73, 627, 1929). The activity was about ⅔ that of the Control using only protease.

The advantages of the present invention will be described below.

(1) In conventional methods of immobilizing enzymes or microorganisms by enclosure, natural carriers such as agar, carrageenan, or calcium alginate are used. However, when compared to Xanthan gum and derivatives thereof, agar and carrageenan may have inferior acid and salt resistance. In addition, these substances are insoluble or difficult to dissolve in water at room temperature; they can only be dissolved in water at 70° to 90° C. or higher. In contrast to this, Xanthan gum and its derivatives are safe, natural products and have various advantages such as good particle dispersion, good solubility in cold water, and excellent stability against temperature changes, various salts, pH changes, enzymes, and extreme temperatures (Xanthan gum and/or water-insoluble salts of its derivatives have good heat stability and do not undergo any change in solubility in warm water at 60° to 70° C.). Xanthan gum and its derivatives are therefore free from the disadvantages of conventional natural immobilizing carriers.

Immobilized microorganisms obtained by the method of the present invention have lower water separation tendencies (of obtained gels) than do natural gels. Therefore, microorganisms immobilized by the present invention can enclose gel culture medium suitable for microoriganism propagation. In this manner, when useful materials are produced by microorganisms, these microorganisms need not be purely cultured every time as the life of the immobilized materials is long, and durability is high.

(2) In the culture, difficulty in removing microorganisms from the culture solution, experienced in the conventional methods, is not encountered.

(3) In the conventional use of calcium alginate, sodium alginate as a raw material is sterilized at high temperature and pressure in an autoclave or the like. Upon this treatment, however, the degree of polymerization of sodium alginate changes, the viscosity of the aqueous solution varies, and its handling is difficult. These problems are not encountered with Xanthan gum and its derivatives.

(4) Substances immobilized by the method of the present invention can be used in aqueous reactions or in reactions using organic solvents. In addition, the immobilized substances can be used as bioreactors by packing them in a column packed tower or the like and having the reaction solution flow continuously therethrough. Due to excellent heat stability, substances obtained by immobilizing heat-resistant microorganisms can be used as catalysts for high temperature reactions.

What is claimed is:

1. A method of immobilizing a biochemically active substance, consisting essentially of: mixing a first aqueous solution containing at least one biochemically active substance and an immobilizing agent selected from the group consisting of xanthan gum and derivatives thereof with a second aqueous solution containing metal ions having a valence of 3 or more, selected from the group consisting of iron, tin, manganese and titanium ions in an amount sufficient to precipitate the xanthan gum or derivatives thereof and obtain a precipitate containing the biochemically active substance immobilized therein.

2. A method according to claim 1, wherein said biochemically active substance is an enzyme.

3. A method according to claim 1, wherein said biochemically active substance is a microorganism.

4. A method according to claim 1, wherein said first aqueous solution contains the immobilizing agent at a concentration of 0.01 to 15%.

5. A method according to claim 1, wherein said first aqueous solution contains the immobilizing agent at a concentration of 0.5 to 7%.

6. A method according to claim 4, wherein said second aqueous solution contains the metal ions at a concentration of 0.01 to 20%.

7. A method according to claim 6, wherein said metal ions are iron ions.

8. A method according to claim 1, wherein said mixing comprises dripping said first aqueous solution into said second aqueous solution.

9. A method according to claim 1, wherein said mixing comprises spraying said first aqueous solution into said second aqueous solution through a thin nozzle.

10. A method according to claim 1, wherein the metal ion is iron ion.

11. A method according to claim 1, wherein the mixing is carried out at a temperature of 5° C. to 75° C.

* * * * *